United States Patent [19]

Hugelier et al.

[11] Patent Number: 5,193,397
[45] Date of Patent: Mar. 16, 1993

[54] GRIP FOR TENSILE TESTS

[75] Inventors: Luc Hugelier, Deerlijk; Marc Devlaminck, Hulste, both of Belgium

[73] Assignee: N.V. Bekaert S.A., Zwevegem, Belgium

[21] Appl. No.: 764,676

[22] Filed: Sep. 25, 1991

[30] Foreign Application Priority Data

Oct. 11, 1990 [BE] Belgium ............................ 09000959

[51] Int. Cl.$^5$ ............................................. G01N 3/08
[52] U.S. Cl. ................................................. 73/833
[58] Field of Search ............................ 73/856–860, 73/831, 833; 269/103, 257–285; 279/102, 104, 105

[56] References Cited

U.S. PATENT DOCUMENTS

| | | | |
|---|---|---|---|
| 213,586 | 3/1879 | Olsen | 73/859 |
| 1,872,047 | 8/1932 | Templin | 73/859 |
| 2,583,885 | 1/1952 | Russenberger | 73/860 |
| 2,676,381 | 4/1954 | Holmes | 73/859 |
| 3,079,789 | 3/1963 | Dean | 73/93 |
| 3,247,742 | 4/1966 | Woodbury | 269/257 |
| 3,745,638 | 7/1973 | Minera | 269/271 |
| 4,537,080 | 8/1985 | Christiansen | 73/857 |

FOREIGN PATENT DOCUMENTS 0047941 3/1985 Japan ................................... 73/856

OTHER PUBLICATIONS

*Journal of Physics E; Scientific Instruments*, "Simple, Light-Weight Grips for Tensile Testing," p. 513, Jan. 11, 1973.
MTS Brochure, "Grips and Fixtures Catalog", MTS Systems Loop, Minneapolis, Minn., 1986.

*Primary Examiner*—Robert Raevis
*Attorney, Agent, or Firm*—Foley & Lardner

[57] ABSTRACT

A grip for the performance of tensile tests on elongated specimens such as steel wires, wherein at least the face of the grip which has an engagement with the elongated specimen is provided with roughnesses. These roughnesses are virtual pyramids in shape, which at no point show an angle which is smaller than 100°. For preference the roughnesses have the form of truncated pyramids with an upper surface area of at least 0.0025 mm$^2$. Wear and breakages in the grip are considerably reduced.

10 Claims, 3 Drawing Sheets

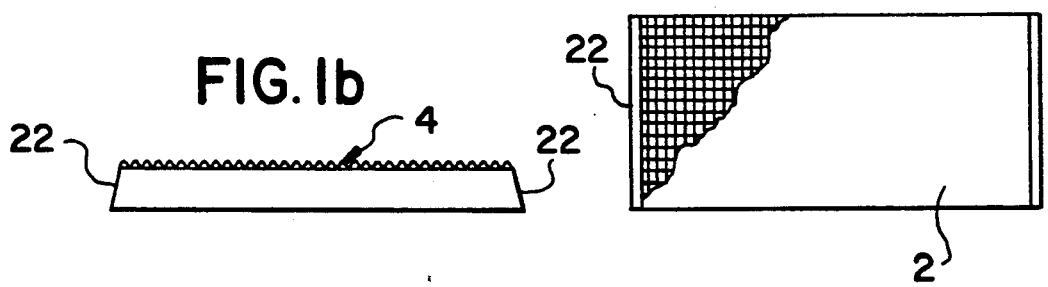
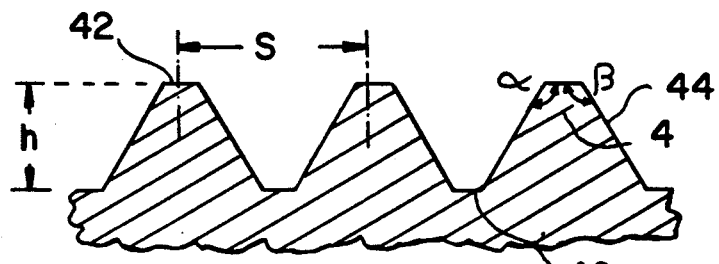
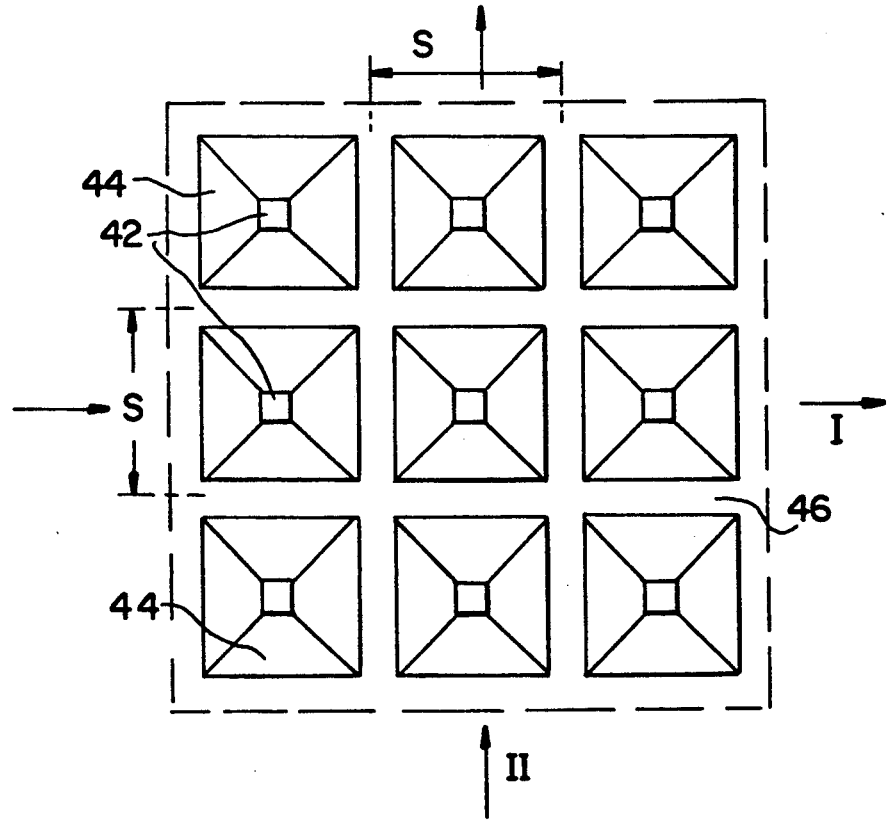

GRIP FOR TENSILE TESTS

BACKGROUND OF THE INVENTION

The invention relates to a grip for the performance of tensile tests on elongated specimens, wherein in at least the face of the grip which engaged with the elongated specimen roughnesses are applied. The invention also relates to a grip holder and a tensile testing apparatus incorporating such a grip.

By roughnesses is meant areas which protrude with respect to the plane of the grip.

The elongated specimens are characterized by a dimension in the longitudinal direction which is many times greater than the dimensions of the cross-section. Examples of such elongated specimens are wires, cables and cords Such elongated specimens are very frequently subjected to tensile tests to determine the tensile strength, breaking strength and other parameters such as elongation, constriction, etc. To this end a certain length of an elongated specimen is gripped in the grip at both ends and subjected to an increasing tensile force until the elongated specimen breaks.

Despite repeated efforts in the past, the grips with which the elongated specimen are gripped continue to create problems.

A first problem occurs particularly during the testing of hard wires such as oil-hardened steel wires. In these tests, the grip is subject to severe wear and requires replacement after only ten tests have been performed This leads to a higher cost due to the high consumption of grips In addition, time is lost in the replacement of grips.

A second problem is the problem of breakages in the grip. The specimen to be tested, for example a steel wire, breaks inside the grip or just outside it. The tensile strength at which this occurs is not necessarily indicative of the actual tensile strength of the specimen, with the result that the tensile test is not reliable and has to be repeated.

In the present state of the art attempts have already been made to substitute the material from which the grips are made with a harder material which would be more resistant to wear. This has not, however, always led to more favourable results since the roughnesses on the grip, due to the extra hardness of the material, are also more brittle, break off more easily and lead to more rapid wear.

OBJECT AND SUMMARY OF THE INVENTION

The invention has as its object to provide a grip which is more resistant to wear and which is less likely to lead to breakages in the grip.

In accordance with a first aspect of the invention, the invention provides a grip for the performance of tensile tests on elongated specimens, wherein, in at least the face of the grip which has an engagement with the elongated specimen, roughnesses or gripping projections are provided. These roughnesses or gripping projections have virtually the form of pyramids or cones whose tops at no point have angles which are greater than 100°, being for example 110° or 120°.

Due to the absence of sharp angles, the stress concentrations between the roughnesses are smaller, which leads to less wear.

Preferably, the roughnesses and the rest of the grip are of one and the same material and form one unity.

The roughnesses preferably have the form of a truncated pyramid or cone with an upper surface area of at least 0.0025 mm$^2$, for example at least 0.0100 mm$^2$.

These slightly flattened roughnesses give rise to still less wear and to fewer breakages of the specimen inside the grip or just outside it.

The roughnesses are preferably arranged in a regular pattern of rows and columns. The distance between the center point of two adjacent roughnesses is preferably smaller than 0.8 mm, and for preference smaller than 0.6 mm, for example 0.4 mm.

In a preferred embodiment the height of the roughnesses is no greater than 0.3 mm, for example no greater than 0.25 mm For steel wires with a diameter of less than 6.5 mm, the optimum distance between the center points of two adjacent roughnesses is virtually 0.5 mm and the optimum height of the roughnesses is virtually 0.2 mm.

In another preferred embodiment, the face of the grip which has an engagement with the elongated specimen is rectangular in shape and the rows and columns of roughnesses are perpendicular to each other and are at all times parallel to one of the sides of the rectangle.

It is also advantageous if the height of the roughnesses gradually reduces towards the longitudinal ends of the grip The grip is preferably made from a material with a Rockwell C hardness of at least 60.

In accordance with a second aspect, the invention provides a grip holder incorporating at least one grip as described above.

In accordance with a third aspect, the invention provides a tensile testing apparatus incorporating at least one grip as described above.

BRIEF DESCRIPTION OF THE DRAWINGS

The invention will now be described in more detail with the aid of the figures, wherein:

FIG. 1(a) is a plan view of a grip according to the invention;

FIG. 1(b) is a cross-sectional view of a grip according to the invention;

FIG. 2(a) is a cross-sectional view of roughnesses or gripping projections of the grip;

FIG. 2(b) is an enlarged plan view of roughnesses or gripping projections of a grip according to the invention;

DETAILED DESCRIPTION OF THE PREFERRED EMBODIMENTS

Figure 3A:
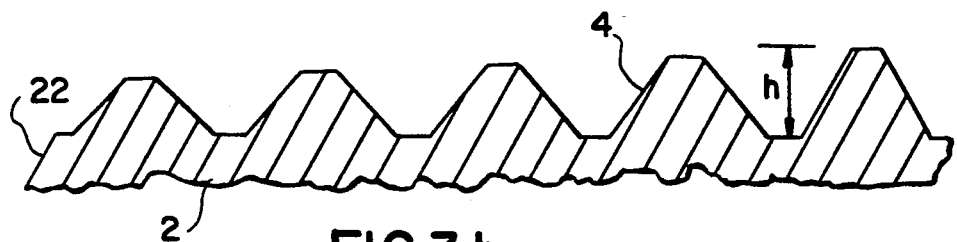
FIGS. 3(a) and 3(b) are cross-sectional views of roughnesses or gripping projections of alternative embodiments of a grip according to the invention.

FIG. 1 shows a grip 2 according to the invention. The longitudinal ends 22 of the grip 2 are bevelled so as to be able to sit securely in a grip holder. The length of such a grip for steel wires with a diameter of less than 6.5 mm may vary from 3.5 cm to 10 cm. The width varies from 1.5 cm to 4 cm. The upper face of the grip 2 is provided with roughnesses or gripping projections 4 which are shown enlarged in FIG. 2.

Referring to FIG. 2, the roughnesses or gripping projections 4 have the form of a truncated pyramid. The upper surface area 42 is larger than 0.0025 mm$^2$, for example 0.0100 mm$^2$. The side faces 44 flare out in the direction of the base to the grooves 46. The distance s between the center lines of two adjacent 4 rows of projections is less than 0.8 mm and, in the illustrated embodiment equals 0.5 mm and the height h of the roughnesses is less than 0.3 mm and, in the illustrated embodiment, equals 0.2 mm. The angles $\alpha$ and $\beta$ between the side faces 44 and the upper surface 42 is greater than 100° and, in the illustrated embodiment, equal 130°. The grip 4 is made from a steel and is treated in such a way that it has a Rockwell C hardness of 66. A possible steel composition is 1.25% C, 4.1% Cr, 3.1% Mo, 9.0% W, 9.0% Co, 3.1% V, the rest consisting of iron and certain impurities.

Such a profile of truncated pyramids can be obtained, for example, by passing a steel plate under an abrasive wheel with a suitable profile, first in direction (I), and then in a direction (II) which is at right angles to direction (I)

FIG. 3 shows a cross-sectional view of an alternative embodiment of a grip 2 in which the height h of the truncated pyramids 4 gradually decreases towards the longitudinal end 22 of the grip.

Figure 4:
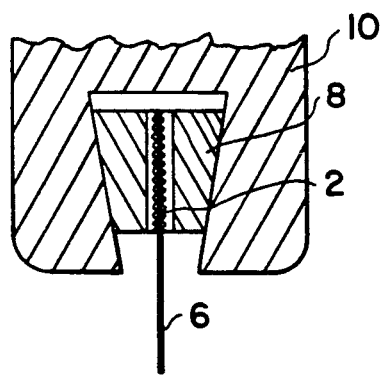
FIG. 4 shows a grip holder with a grip according to the invention.

FIG. 4 shows how a grip 2 can be mounted in a grip holder 10 by means of an intermediate fitting 8. As the tensile force on the wire 6 increases, the conical shape of the intermediate fitting 8 and the grip holder 10 causes an increase in the transverse force on the wire 6.

Figure 5:
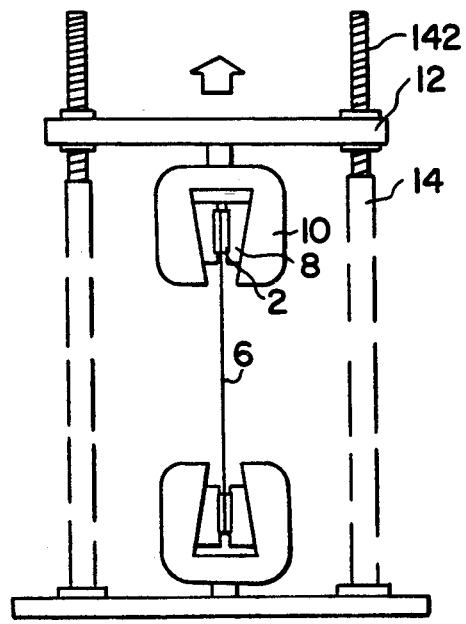
FIG. 5 shows an apparatus for the performance of tensile tests.

FIG. 5 shows a complete tensile testing apparatus. The lower grip holder 10 is connected to the frame. The upper grip holder 10 is connected to a crosshead 12 this crosshead 12 is movably connected to the 14. The jacks 14 have a helical profile 142 such that when the jacks rotate the crosshead 12 moves upwards or downwards. During the upward movement, tensile force is exerted on the wire 6.

An explanation of why the grips described above give rise to less wear and grip breakages can be given as follows.

Figure 6A:
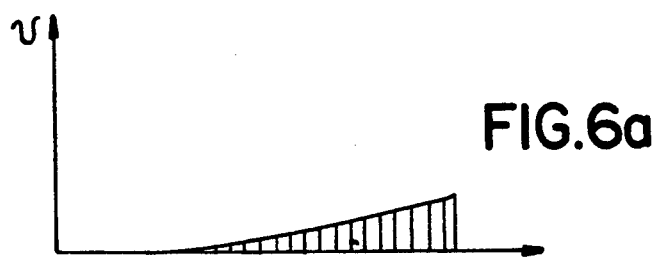
FIG. 6(a) shows the relative movement of the elongated specimen with respect to the grip.

FIG. 6(a) shows the relative movement of the wire 6 with respect to the grip 2. At the end of the wire 6 the relative movement is non-existent because the anchorage of the wire 6 in the grips 2 is complete at that point The non-gripped section of the wire 6 undergoes relative movement during a tensile test with respect to the grips 2. This relative movement must not fall to zero too suddenly at the point where gripping begins, but must be able to reduce continuously as the anchorage increases.

Figure 6B:
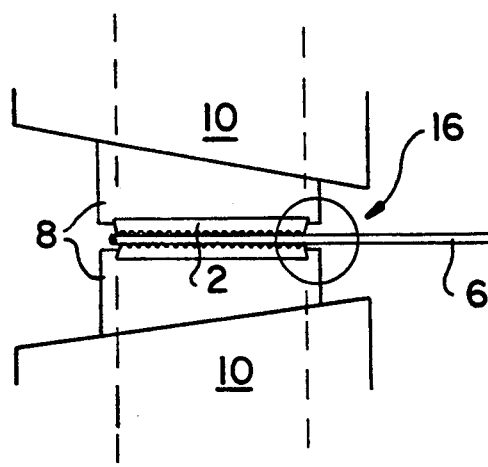
FIG. 6(b) shows schematically an elongated specimen in a grip and grip holder.
Figure 6C:
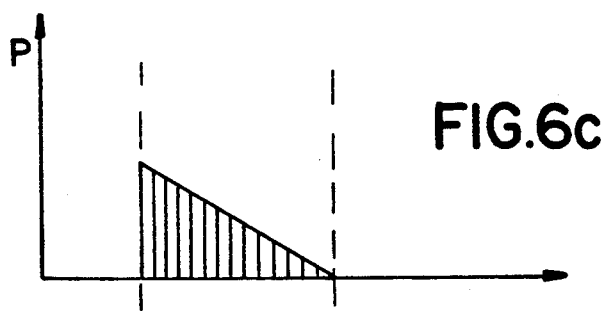
FIG. 6(c) shows the profile of the pressure along the gripped elongated specimen.

FIG. 6(c) shows the pressure p imposed in the gripper section of the wire. This pressure p increases over the length of the gripped section of the wire 6.

Figure 6D:
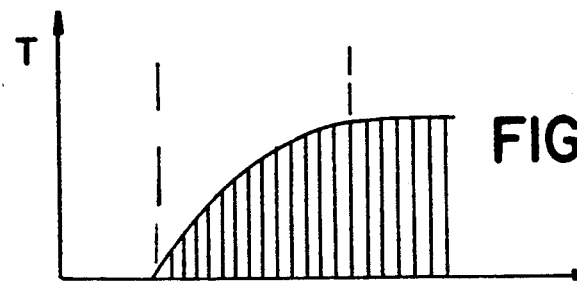
FIG. 6(d) shows the profile of the tensile force in the elongated specimen.

FIG. 6(d) shows the tensile force T in the wire 6. This tensile force T is proportional to the integral of the pressure p and to a friction coefficient.

From the above it follows that the most critical zone of the grip 2 is located at the end where the wire 6 begins to be gripped. This zone is shown in FIG. 6(b) enclosed by a circle 16. In this zone the wire 6 has a tendency to move with respect to the grip while the tensile force in the wire 6 is at its greatest at that point. In this zone the roughnesses 4 of the grip are subject to the greatest load.

If these roughnesses 4 are sharp and if they bite deeply into the wire 6, then these roughnesses 4 permit no relative movement of the wire with respect to the grip and the load on both these roughnesses and on the wire is extremely high in the critical zone 16. Either the wire 6 breaks in the grip just outside it—the actual cross-sectional area of the wire has become smaller due to the penetration of the roughnesses—or a roughness 4 breaks off, following which other neighbouring roughnesses also break off because they then are subjected to all the loads.

If, in contrast, the tops of the roughnesses or gripping projections 4 have no sharp angles or points, as is the case in the invention, they also do not penetrate deeply into the wire 6 and the stresses which arise both in the wire 6 and in the roughnesses 4 are less great, which gives rise to less wear and less breaks in the grip. If, moreover, the tops of the roughnesses are slightly flattened or rounded, then the relative movement between the wire 6 and the grip 2 is not stopped suddenly, the gripping also increases gradually and the stresses do not become so high.

If the roughnesses are fairly close together (s<0.8 mm), then gripping can be effected by several roughnesses instead of by only a few roughnesses, and in this way the stresses are distributed.

If the height of the roughnesses is limited (h<0.4 mm), then the roughnesses penetrate less deeply into the wire, which also gives rise to fewer stresses both in the roughnesses and in the wire.

Figure 3B:
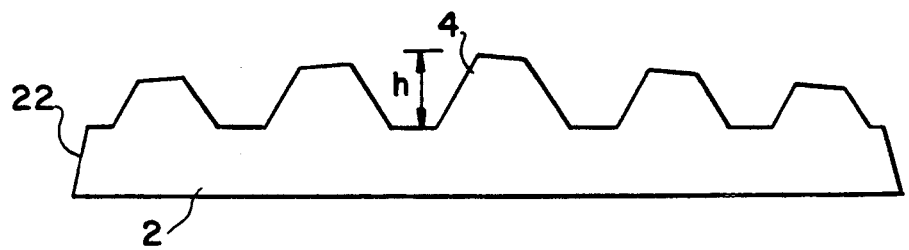

If the upper side of the grip is rectangular and if the rows and columns of roughnesses or gripped projections are always parallel to one of the sides of the grip, then the wire 6 can locate in a groove 46 of the grip profile during a tensile test. The wire 6 is then 'supported' by the side faces 44 which at no point penetrate the wire and at no point give rise to stress peaks. If the grip has roughnesses or gripped projections whose heights decrease towards the longitudinal end of the grip, then it will also be clear from the above that the chance of grip breakages or breaking off of the roughnesses is substantially reduced. Alternatively, the heights of the roughnesses or gripping projections may decrease towards the longitudinal ends of the grip, as illustrated in FIG. 3(b).

Tests have shown that, by using a grip according to the invention, the number of breakages of the steel wire in the grip or just outside it is reduced from 1 in 3 to 3 in 100.

Tests have also shown that the grip according to the invention can be used for 300 tensile tests on oil-hardened steel wires, an application in which a grip according to the present state of the art had to be replaced after only twenty tests.

The invention is not limited to one grip with a single face provided with roughnesses, but can also be applied to a grip with, for example, a V-shaped groove in which the two faces of the groove are at least partially covered with roughnesses.

We claim:

1. An apparatus comprising:
 a grip for performing tensile tests on elongated specimens, said grip having at least one face for engaging said elongated specimens, said face having gripping projections which are arranged in a regular pattern of rows and columns and which have the form of truncated pyramids each having side faces and a flat upper surface, wherein the distance between center lines of adjacent rows columns of said gripping projections is less than 0.8 mm.

2. A grip according to claim 1, wherein each of said gripping projections has a height which is less than 0.3 mm.

3. A grip according to claim 1, wherein said face is in the form of a rectangle and wherein one of said rows and said columns are parallel to tone side of said rectangle.

4. A grip according to claim 1, wherein an angle between the side faces and the upper surface of each of said gripping projections is grater than 100°.

5. A grip according to claim 1, wherein all components of said grip are made from the same material and form an integral unit.

6. A grip according to claim 1, wherein the upper surface of each of said gripping projections has an area of at least 0.0025 mm$^2$.

7. A grip according to claim 1, wherein said grip has longitudinal ends, and wherein the heights of said gripping projections gradually decrease towards said longitudinal ends of said grip.

8. A grip according to claim 1, wherein said grip is made form steel having a Rockwell C hardness which is greater than 60.

9. An apparatus comprising:
 a grip holder incorporating at least one grip, said grip including at least one face, said face having gripping projections which are arranged in a regular pattern of rows and columns and which have the form of truncated pyramids each having side faces and a flat upper surface, wherein the distance between center lines of adjacent rows and columns of said gripping projections is less than 0.8 mm.

10. An apparatus comprising:
 a tensile testing apparatus incorporating at least one grip, said grip including at least one face for engaging elongated specimens, said face having gripping projections which are arranged in a regular pattern of rows and columns and which have the form of truncated pyramids each having side faces and a flat upper surface, wherein the distance between center lines of adjacent rows and columns of said gripping projections is less than 0.8 mm.

* * * * *